United States Patent
Karakasoglu et al.

(10) Patent No.: US 6,171,258 B1
(45) Date of Patent: Jan. 9, 2001

(54) MULTI-CHANNEL SELF-CONTAINED APPARATUS AND METHOD FOR DIAGNOSIS OF SLEEP DISORDERS

(75) Inventors: Ahmet Karakasoglu, San Francisco; Karl S. Johnson, Palo Alto; John Scott Adams, Los Gatos, all of CA (US)

(73) Assignee: Sleep Solutions, Inc., San Jose, CA (US)

( * ) Notice: Under 35 U.S.C. 154(b), the term of this patent shall be extended for 0 days.

(21) Appl. No.: 09/169,780

(22) Filed: Oct. 8, 1998

(51) Int. Cl.[7] .......................................... A61B 5/00
(52) U.S. Cl. ............................ 600/529; 600/538
(58) Field of Search ................................ 600/300, 459, 600/481–486, 500–508, 529–538; 128/897–898

(56) References Cited

U.S. PATENT DOCUMENTS

| | | | |
|---|---|---|---|
| 4,129,125 | 12/1978 | Lester et al. | 128/715 X |
| 4,862,144 | 8/1989 | Tao | 128/721 X |
| 4,956,867 | 9/1990 | Zurek et al. | |
| 5,353,788 | * 10/1994 | Miles | 128/204.23 |
| 5,385,144 | 1/1995 | Yamanishi et al. | 128/633 X |
| 5,522,382 | * 6/1996 | Sullivan et al. | 128/204.23 |
| 5,522,862 | * 6/1996 | Testerman et al. | 607/42 |
| 5,784,300 | * 7/1998 | Neumeier et al. | 364/574 |

* cited by examiner

*Primary Examiner*—Max Hindenburg
*Assistant Examiner*—Michael Astorino
(74) *Attorney, Agent, or Firm*—Harold C. Hohbach; Flehr Hohbach Test Albritton & Herbert LLP

(57) ABSTRACT

A sleep monitoring apparatus adapted to be mounted on a human head of a patient having a front face and first and second sides with the front face having a mouth, a nose with nostrils therein and first and second eyes and first and second ears on the first and second sides comprising a movable headpiece adapted to be mounted on the head and engages the head above the eyes. An acoustical device is provided which is adapted to be positioned on the face in the vicinity of the nose and/or mouth of the patient and having at least one acoustic duct from receiving respiratory airflow from the patient. A sensor which is exposed to the acoustic duct is provided for sensing turbulence and/or pressure changes in the respiratory airflow in the acoustic duct and providing an electrical output. Electrical circuitry is carried by the headpiece for receiving the electrical output and for processing the electrical output to provide a real-time signal from the headpiece which is indicative of the breathing of the patient.

22 Claims, 2 Drawing Sheets

MULTI-CHANNEL SELF-CONTAINED APPARATUS AND METHOD FOR DIAGNOSIS OF SLEEP DISORDERS

This invention relates to a multi-channel self-contained apparatus and method for diagnosis of sleep disorders.

Attempts have heretofore been made to diagnose sleep disorders utilizing various devices and methods. Typically these have been utilized in sleep clinics in which the patient must come into the sleep clinic. Such apparatus and methods have not been particularly suitable for unattended home studies. There is therefore a need for a sleep monitoring apparatus which can be utilized for unattended home studies of sleep disorders.

In general, it is an object of the present invention to provide a self-contained apparatus and method for diagnosis of sleep disorders which can be used in connection with unattended home studies.

Another object of the invention is to provide an apparatus and method of the above character in which multiple channels of information are utilized.

Another object of the invention is to provide an apparatus which is self-contained.

Another object of the invention is to provide an apparatus and method of the above character which includes sensors for picking up brain waves.

Another object of the invention is to provide an apparatus and method of the above character which includes sensors for detecting eye movement.

Another object of the invention is to provide an apparatus of the above character which can be worn on the person of the human being.

Another object of the invention is to provide an apparatus of the above character which can be incorporated into a headpiece for the patient.

Another object of the invention is to provide an apparatus of the above character which can be incorporated into a headband for the patient.

Another object of the invention is to provide an apparatus of the above character which includes a sensor for measuring oxygen desaturation.

Another object of the invention is to provide an apparatus of the above character in which the sensor is provided for determining body position.

Another object of the invention is to provide an apparatus and method of the above character for providing a respiratory disturbance index for a sleep disorder.

Another object of the invention is to provide an apparatus and method of the above character which makes it possible to provide an augmented respiratory disturbance index.

Another object of the invention is to provide an apparatus and method of the above character in which ambient sound pickup is minimized.

Another object of the invention is to provide an apparatus and method of the above character in which respiration signals of improved quality are achieved which are substantially immune to ambient sound permitting the amplification of respiratory sounds to facilitate detection of shallow breathing.

Another object of the invention is to provide an apparatus and method of the above character in which a Helmholtz resonator is utilized to achieve substantial immunity from ambient sound.

Another object of the invention is to provide an apparatus and method of the above character in which a Helmholtz resonator is utilized having a selected frequency which is above the audible range of the human ear.

Another object of the invention is to provide an apparatus and method of the above character in which a self-contained real time automatic scoring system is utilized.

Additional features and objects of the invention will appear from the following description in which the preferred embodiments are set forth in the accompanying drawings.

In general, the sleep monitoring apparatus is adapted to be mounted on a patient having a head with a front face and first and second sides with the face having a mouth, a nose with nostrils therein overlying the mouth, first and second eyes spaced apart above the nose and first and second ears on the first and second sides. A removable headpiece is adapted to be mounted on the head so that it engages the head above the eyes. An acoustical device is adapted to be positioned on the face in the vicinity of the nose and/or mouth of the patient and has at least one acoustic duct receiving respiratory airflow from the patient. A sensor is exposed to the acoustic duct for sensing turbulence and/or pressure changes in the respiratory airflow in the acoustic duct and providing an electrical output signal. Electrical circuitry is carried by the headpiece for receiving the electrical output and for processing the electrical signal to provide a real time signal from the headpiece which is indicative of breathing of the patient.

Figure 1:
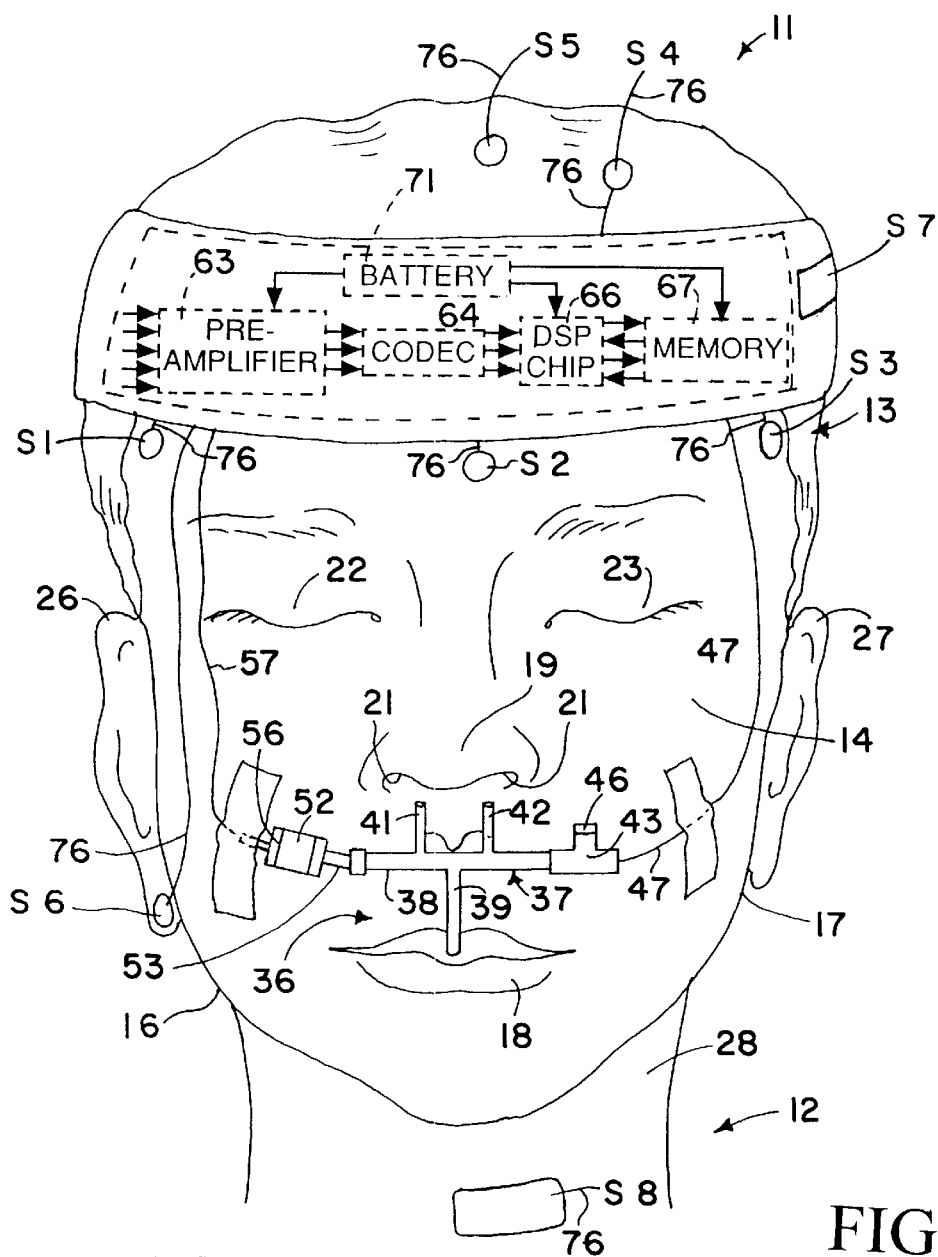
FIG. 1 is a front elevational view of an apparatus incorporating the present invention mounted on the head of a human being or patient.
Figure 2:
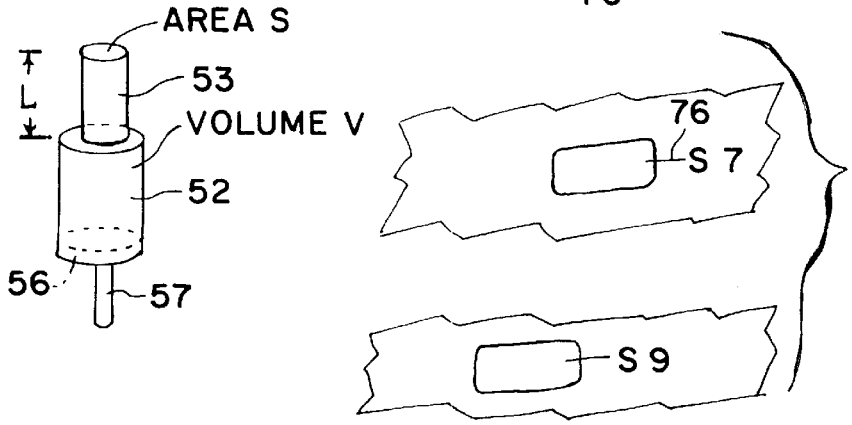
FIG. 2 is an isometric front elevational view of the Helmholtz resonator shown in FIG. 1.

More particularly as shown in FIG. 1 of the drawings, the sleep monitoring apparatus 11 which alternatively can be called apparatus for diagnosis of sleep disorders is shown mounted on a patient 12 having a head 13 with a front face 14 and first and second sides 16 and 17. The face has a mouth 18. A nose 19 is positioned above the mouth 18 and has first and second nostrils 21 therein facing downwardly toward the mouth 18. First and second eyes 22 and 23 are positioned above the nose and are spaced apart on opposite sides of the nose. First and second ears 26 and 27 are provided on the opposite sides 16 and 17. A neck 28 is provided for supporting the head 13 on the body (not shown) of the patient.

The apparatus 11 includes a removable headpiece 31 which is to be mounted on or carried by the head of the patient. As shown the headpiece 31 is in the form of a headband of the type typically worn by athletes. Such a headband as is well known to those skilled in the art can consist of cotton fibers which have been knitted into a band having a certain width as for example 1½" and having a size such that it can be fitted snugly on the head of the patient. If desired, the headband can include certain elastic fibers or elements (not shown) to impart stretchability to the headpiece and to aid in retention of the headpiece 31 on the head 13 of the patient. The apparatus also includes an acoustical device 36 which is adapted to be positioned on the face of the patient in the vicinity of the nose and/or the mouth of the patient.

This acoustical device 36 can generally be of the type described in co-pending application Ser. No. 09/169,776 filed Oct. 28, 1998. As disclosed therein, the acoustical device 36 is formed of a single body 37 of a suitable medical grade plastic such as polyurethane, polyvinyl chloride and silicone. The body 37 is relatively flexible so that it can accommodate the contours of the face of the patient to be comfortable to the patient while being worn by the patient.

The body 37 consists of elongate tubular portion 38 which is generally disposed in a horizontal position on the face 14. It is provided with a depending portion 39 extending at substantially right angles to the horizontal tubular portion 38 and having its lowermost extremity in the vicinity of the mouth 18 of the patient. Spaced apart upstanding tubular portions 42 and 42 are positioned so that they underlie the nostrils 21 of the nose 19 of the patient. As described in co-pending application Ser. No. 09/169,776 filed Oct. 28, 1998, the horizontal tubular portion 38, the depending portion 39 and the upstanding tubular portions 41 and 42 have acoustic flow passages therein which are in intercommunication with each other. Another upstanding tubular portion 43 is provided on the horizontal tubular portion 38 and is in communication with the flow passage therein. A sensor in the form of a microphone 46 is disposed in the upstanding tubular portion 43 to measure ambient sounds in the vicinity of the head of the patient as well as snoring and breathing sounds of the patient. The microphone 46 acts as a respiratory sound sensor which is dedicated to sense sound intensity in dB. The microphone 46 is connected by wires (not shown) provided in a cable 47. The cable 47 is connected into electronics and electrical circuitry provided in the headpiece 31 as hereinafter described.

Another sensor 51 is carried by the body 37 and takes the form of an acoustic cavity resonator 51 often called a "Helmholtz" resonator mounted on one end of the horizontal tubular portion 38 of the body 37 generally opposite the end in which the sensor 46 is mounted. The Helmholtz resonator is of a type well known to those skilled in the art and typically is provided with a closed cylinder 52 having closed ends providing a closed volume or cavity "V" and which has a centrally disposed straight tube in the form of a stem or neck 53 having a length "l" and a cross sectional area "S" extending out of one end of the cylinder and of a smaller diameter than the cylinder 52. The stem 53 is provided with an open end and is mounted in one end of the horizontal tubular portion 38 with the flow passage in the horizontal tubular portion 38 in communication with the open end of the stem 53. Typically in a Helmholtz resonator the resonant frequency $f_o$ is determined in accordance with the following equation:

$$f_0 = \frac{1}{2\pi}\sqrt{\frac{c^2 S}{l_e V}} \qquad \text{Equation 1}$$

where $c$ = speed of sound $S$ = cross-sectional area of tube $V$ = closed volume $f_0$ = resonant frequency $l_e$ = effective length of tube 53 approximately $1 + 0.8\sqrt{S}$.

Utilizing this equation, the resonator 51 was designed to have a resonant frequency $f_o$=27 kHz in which V was from a cylinder 52 having a diameter of I.D. 0.25" and a height of 0.2" to 0.6" and the stem 53 having a diameter of I.D. 0.13" and a length of 0.4" to 0.8".

A microphone 56 is mounted in the cylinder 52 opposite the stem 53 and is provided for picking up the resonant frequency created within the resonator 51. The Helmholtz resonator 51 is formed of a suitable metal as for example stainless steel to form a rigid cavity. The microphone 56 can be a relatively inexpensive microphone because it needs to only sense the narrow frequency band for which the resonator has been designed. Thus by way of example in connection with the present invention, a resonator was selected having a resonant frequency of 27 Khz. This frequency in accordance with the Equation 1 set forth above is determined by the surface area and the total volume of the sensor. It is the ratio of these two factors which is important. The resonator can be scaled proportionally to provide the same resonant frequency. Other frequencies can be utilized as for example from 20–40 Khz. The Helmholtz resonator is utilized for generating tonal sounds of basically a single frequency.

In connection with the present invention, it is desirable to select a frequency which is above the frequency which normally can be heard by the human ear which is typically between 17–18 KHz. The frequency of 27 KHz was selected so that it would be significantly above this audible range of the human ear. In addition this frequency was selected so that most ambient sounds are screened out because typically ambient sounds are of a low frequency and substantially below 27 Khz. Since the Helmholtz resonator 51 is formed of steel, it in addition to generating the single tonal frequency suppresses low frequencies because of its construction. Thus the Helmholtz resonator 51 amplifies respiratory sounds which are picked up by the microphone 56 in the resonator 51 while at the same time suppressing or attenuating ambient sounds. The resonator 51 converts the airflow around the opening of the cavity to a narrow band acoustic signal around the resonance frequency of the oscillator. The ambient sounds are attenuated in traveling through the air/solid interface of the rigid cavity. With the microphone 56 in the rigid cavity, a natural low pass filter is obtained which will suppress the high frequency components of the background noise while the breathing sounds are not suppressed. For example, the background noise can be attenuated as much as 45 dB around 10 Khz. The ambient sounds at lower frequencies are substantially removed by an active noise canceler as hereinafter described. Conductors (not shown) are connected to the microphone 56 and extend through a cable 57 connected to the electronics provided in the headpiece 37 as hereinafter described.

The cables 47 and 57 are connected into electronic circuitry 61 carried by the headpiece 31. The electronic circuitry 61 as shown is provided in the headpiece 31 in the form of a headband. The circuitry is comprised of a plurality of components which are mounted on a flexible circuit board 62. The surface mounted components as shown particularly in FIG. 1 include a preamplifier 63, a CODEC 64, a DSP chip 66 and a memory 67. The circuitry 61 also includes its own internal battery 71 so that the electronic circuitry carried by the headpiece 31 is a self-contained self-sufficient device. The surface mounted components 63, 64, 66 and 67 provided on the flexible circuit board 62 are designed to utilize as little power as possible.

It should be appreciated, however, that in connection with the present invention, the circuitry provided in the headpiece 31 can be limited to that required for collecting information from the sensors as for example the sensors 46 and 51 as well as other sensors hereinafter described. This collected information can be transmitted from a small transmitter (not shown) also carried by the headpiece 31 and then transferred the same through an antenna to another antenna carried by a receiver in a remote location as for example on a night stand (not shown) close to the bed of the patient.

In connection with the present invention it often is desirable to include additional sensors other than the ones which are dedicated to picking up breathing and snoring sounds as well as picking up ambient sounds. Thus, in accordance with the present invention, it may be desirable to pick up additional channels of information which will make the present apparatus more suitable for the diagnosis of sleep disorders. For example it often is desirable to provide channels of information which can be utilized for ascertaining sleep staging. Thus electroencephalogram (EEG) signals can be picked up from the patient to ascertain the brain waves being generated by the patient as well as electrooculogram (EOG) and electromyogram (EMG) signals. Thus, there has been provided sensors S1 through S7 in which S1 through S5 are mounted on the scalp and forehead. Sensor S2 is a reference sensor and is mounted on the forehead above the nose 19. Sensors S1 and S3 are mounted on opposite sides of the eyes 22 and 23 with the sensor S1 being mounted in close proximity to the right eye 22 and the sensor S3 being mounted in close proximity to the left eye 23. Thus sensors S1 and S2 collect information with respect to movement of the eyes.

Sensors S4 and S5 are dedicated for picking up brain signals and are mounted on the scalp as shown in FIG. 1 with sensor S4 being centered over the forehead and immediately above the headpiece 31 and sensor S5 is mounted off to one side generally above the right eye 22 and rearwardly of the right eye 22.

The sensors provided can also include a sensor S6 which is in the form of a pulse oximeter that can be located in a suitable position as for example on the earlobe of the ear 26 of the patient. Such a sensor can operate in a reflective mode and serves as an oxygen desaturation sensor. A body position sensor S7 also can be provided which serves to sense the body position during the sleeping hours of the patient. Such a body position sensor can be located in an appropriate position as for example the chest or a thigh or torso of the patient. It also can be located in an alternative position such as the head of the patient. A tracheal sensor S8 can also be provided and can be located in close proximity to the trachea as for example on the neck 28 of the patient as shown in FIG. 1. This sensor S8 can be in the form of a piezoelectric sensor which senses vibrations of the trachea of the patient. It also can be utilized for sensing the heart rate. Effort being exerted by the patient in breathing can be sensed with an electromyogram (EMG) sensor S9 placed on the abdomen of the patient.

It should be appreciated that the heart rate can be sensed by any one of a number of the sensors provided. Therefore it is unnecessary to provide a dedicated sensor for ascertaining the heart rate. All of the sensors hereinbefore described are connected into the electronic circuitry 61 hereinbefore described by individual cables 76.

Figure 3:
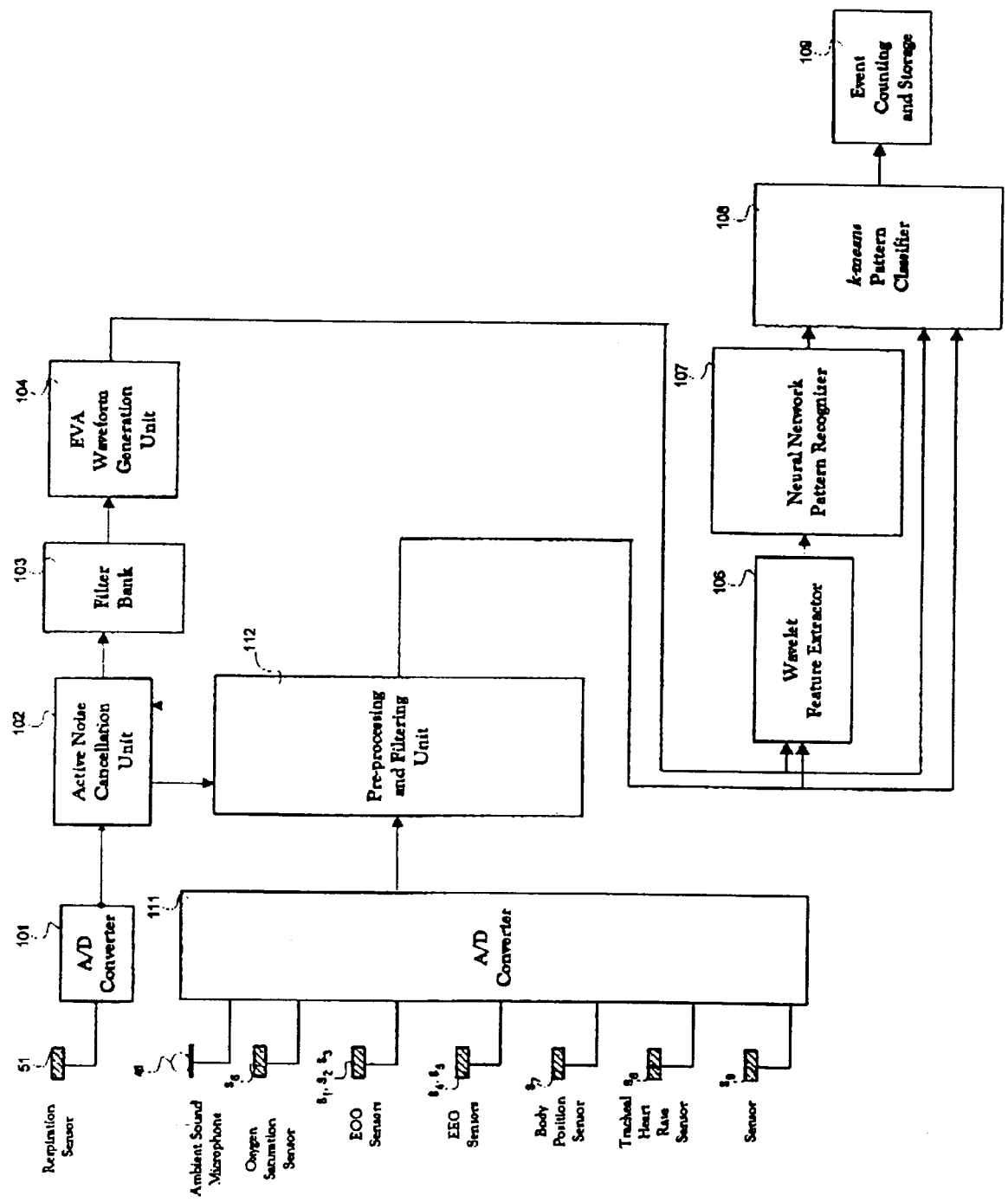
FIG. 3 is a block diagram of the multi-channel diagnostic system utilized in the apparatus.

The electronic circuitry which is shown in FIG. 3 may now be briefly described as follows. In FIG. 3 there is shown a block diagram of the multi-channel headband diagnostic system incorporating the present invention. As shown therein, the respiration sensor in the form of a Helmholtz resonator 51 is shown therein in conjunction with the ambient sound microphone 46, the oxygen saturation sensor S6, the EOG sensors S1 and S3, the EEG sensors S4 and S5, the body position sensor S1 and the tracheal and heart rate sensor S8 and the reference sensor S2.

These various sensors are connected into electronic circuitry shown in FIG. 3 which is of a type similar to that described in application Ser. No. 09/169,781 filed Oct. 28, 1998. As shown in FIG. 3, the respiration sensor 51 is connected to and has its output supplied to an A/D converter 101 that has its output supplied to an active noise cancellation unit 102 in which background noise is suppressed and the useful information i.e. the breathing or snoring sound signals are extracted and supplied to a filter bank 103. The signals are band pass filtered to adjust the band width to a desired signal characteristic to further improve the signal-to-noise ratio. The output of the filter bank 103 is supplied to an estimated volume of airflow (EVA) waveform generation unit 104. The information from the EVA waveform generation unit 104 is supplied to a wavelet feature extractor 106 which has its output supplied to a neural network pattern recognizer 107. The output of the neural network pattern recognizer 107 is supplied to a k-means pattern classifier 108 that has its output connected to an event counting and storage unit 109.

As also shown in FIG. 3, the outputs of the other sensors hereinbefore described are supplied to an A/D converter 111 which has its output supplied to a preprocessing and filtering unit 112 that has its output supplied to the wavelet feature extractor 106, thence through the neural network pattern recognizer 107, the k-means pattern classifier 108, and finally to the event counting and storage unit 109. The event counting and storage unit 109 provides a measure for a sleep disorder index which is called respiratory disturbance index (RDI) by counting the apneas plus hypopneas per hour of the patient being examined. Such an index, however, does not classify an event any differently whether it is 10 seconds or longer prior to cessation or whether there has been a reduction in airflow. Thus a 10 second event is counted the same as a 2 minute event. In order to obtain improved resolution to provide what can be called RDI plus, additional information is measured. In order to achieve this increased resolution, it is necessary to analyze multi-channels of information as for example the channels shown in FIG. 3.

The wavelet feature extractor 106 in accordance with the present invention greatly improves the dynamic range and accuracy of the signals by converting the signals from the EVA waveform generation unit to a logarithmic scale. To obtain a logarithmic scale signal, the EVA signal, f(t), is subjected to the following conversion:

$$d(t)=(1/\log 2)\log[f(t)]=3.2193 \log[f(t)]  \quad\quad \text{Equation 2}$$

which is supplied to the wavelet feature extractor. The wavelet feature extractor provides wavelets which offer an effective tool to analyze transient signals with short time behavior because of their feature extraction capabilities. The continuous-time wavelet transform of the EVA signal f(t) with respect to the wavelet g(t) is defined as $$W_g f(a, b) = \frac{1}{\sqrt{|a|}} \int_{-\infty}^{\infty} f(t) g\left(\frac{t-b}{a}\right) dt \quad\quad \text{Equation 3}$$

where $$g\left(\frac{t-b}{a}\right)$$

is obtained from the mother wavelet g(t) satisfying $$F\{g(t)\} = G(w); \quad \int_{-\infty}^{\infty} \frac{|G(w)|^2}{|w|} < \infty \quad\quad \text{Equation 4}$$

In the present invention the wavelet transform (WT) is used as a pre-processor for the neural network pattern classifier 108. The wavelet decomposition of an EVA cycle is used as an input in order to obtain apnea/hypopnea events. The details of the wavelet feature extractor and the neural network pattern recognizer are described in detail in co-pending application Ser. No. 09/169,781 filed Oct. 28. The neural network therein described is useful in modeling nonlinear mappings. The neural network pattern recognizer of the present invention accepts the EVA waveform and its frequency and determines if a given sound pattern represents a breathing or snoring sound. Breathing and snoring patterns are utilized to train the neural network weights in order to decide if a given sound signal is any kind of breath signal. Polysomnograph airflow curves and published breathing statistics have been employed in the training set for the neural network.

The k-means pattern classifier 108 works in association with the neural network pattern classifier. The distance of the center of gravity point of each given event with the reference events is measured and a decision is made whether the event is a a) healthy breathing event, b) hypopnea event, or c) apnea event.

Standard polysomnograph decisions have been used as reference events when measuring the Euclidean distances that is defined as $$L(t)[(d_1)^2+(d_2)^2+(d_m)^2]^{1/2} \quad \text{Equation 5}$$

When diagnosing sleep-disordered breathing, a respiratory disturbance index (RDI) is commonly used to indicate the severity of the disease. Typically RDI is determined by dividing the total number of disordered events by duration of sleep. These events consist of apneas and hypopneas. Apneas are defined as total cessation of respiratory airflow for at least 10 seconds. A commonly used definition of a hypopnea event is a reduction of respiratory airflow by at least 50% lasting 10 seconds or longer. In addition it may be desirable to require 2–4% oxygen desaturation in addition to the airflow reduction and duration conditions for a hypopnea event. No parameter is used to assess the severity of each event. Thus an event with 50% airflow reduction lasting 10 seconds is treated the same as an event with 80% airflow reduction, lasting 90 seconds.

In accordance with the present invention in order to improve screening capabilities and to provide a better assessment regarding the severity of sleep-disordered breathing, a new measure, an enhanced respiratory index which can be called RDIplus, is utilized. This index emphasizes several aspects of sleep-disordered breathing, like duration, decrease in $SaO_2$ and airflow reduction. The RDIplus can be calculated by dividing the sum of Event Values by duration of sleep where the Event Value is defined as

---

Event Value = $1 + w_d(T - \tau) + w_a(r - p) + w_o(D - \Delta) + w_x A$ Equation 6
where
$T \geq \tau$ is duration of event (measured)
$\tau$ is minimum duration required to qualify for an event (typical value = 10)
$R \geq p$ is percentage of airflow level (measured)
p is minimum percentage of airflow reduction required to qualify for event (typical value = 50%)
$D \geq \Delta$ is $O_2$ desaturation (measured)
$\Delta$ is maximum $O_2$ desaturation allowed (typical value = 2%)
A = 1 if this event contains an arousal, A = 0 else.
$W_d$ is weight of duration (typical value = 0.02)
$W_a$ is weight of airflow reduction (typical value = 0.01)
$w_o$ is weight of $O_2$ desaturation (typical value = 0.05)
$w_x$ is weight of arousal (typical value = 0.2)

---

It has been found that the RDIplus measure is particularly useful for screening devices that utilize a fewer number of channels than that of a typical polysomnograph. As an example, for a single-channel screening device respiratory airflow sensor, the following definition of Event Value can be used:

---

Event Value = $1 + w_d(T - 10) + w_a(50 - r)$ Equation 7
where
$T \geq 10$ sec. is duration of event,
$r \geq 50$ is percentage airflow level,
$w_d$ is weight of duratian (typical value = 0.02),
$w_a$ is weight of airflow reduction level (typical value = 0.01).

---

From the foregoing it can be seen that there has been provided a self-contained real-time automatic-scoring apparatus. It is incorporated into a unique and compact headband design. Advanced signal processing has been utilized in conjunction with a multi-channel input. Pattern recognition utilizing wavelets and neural networks has been provided. A new sleep disorder index, RDIplus, is made possible. The apparatus is ambulatory.

What is claimed is:

1. A self-contained sleep monitoring apparatus adapted to be mounted on and solely carried by the body of a patient having a front face and first and second sides with the front face having a mouth, a nose with nostrils therein and first and second eyes and first and second ears on the first and second sides comprising a removable bodypiece adapted to be mounted on the body of the patient, an acoustical device adapted to be positioned on the face in the vicinity of the nose and/or mouth of the patient and having at least one acoustic space receiving respiratory airflow from the patient, a sensor exposed to the acoustic space for sensing turbulence and/or pressure changes in the respiratory airflow in the acoustic space and providing an electrical output, electrical circuitry carried by the bodypiece and movable with the patient for receiving the electrical output and for processing the electrical output to provide a real-time signal from the bodypiece which is indicative of the breathing of the patient.

2. Apparatus as in claim 1 wherein said removable bodypiece is a headband adapted to be mounted on the head of the patient and engaging the head above the eyes and having stretchable elastic characteristics.

3. Apparatus as in claim 1 wherein a plurality of event values are provided based upon a minimum duration and wherein a respiratory disturbance index plus is ascertained which is based upon the sum of event values divided by the duration of sleep of the patient.

4. Apparatus as in claim 1 wherein said sensor exposed to the acoustical space is a Helmholtz resonator.

5. Apparatus as in claim 4 wherein said Helmholtz resonator has a frequency which is substantially above the frequency range of hearing of the human ear.

6. Apparatus as in claim 5 wherein said resonant frequency has a frequency 27 kilocycles.

7. Apparatus as in claim 4 wherein said Helmholtz resonator is formed of a metal to suppress low frequencies.

8. Apparatus as in claim 4 wherein said sensor includes a microphone mounted in the Helmholtz resonator.

9. Apparatus as in claim 1 further including additional sensors connected to the electrical circuitry.

10. Apparatus as in claim 9 wherein said additional sensors include sensors adapted to be mounted on the head of the patient for picking up EEG signals from the brain of the patient.

11. Apparatus as in claim 9 wherein said additional sensors include sensors adapted to be mounted on the forehead of the patient in the vicinity of the eyes of the patient for ascertaining EOG signals.

12. Apparatus as in claim 9 wherein said additional sensors include a pulse oximeter adapted to be carried by the head of the patient.

13. Apparatus as in claim 9 wherein said additional sensors include a sensor adapted to be mounted on the body of the patient for sensing the body position of the patient.

14. Apparatus as in claim 9 wherein said additional sensors include a sensor adapted to be mounted on the body of the patient external of the body of the patient for sensing vibrations of the trachea of the patient.

15. Apparatus as in claim 9 wherein said additional sensors include a sensor adapted to be mounted on the body of the patient for sensing the heart rate of the patient.

16. Apparatus as in claim 3 wherein said event value has a duration of at least 10 seconds.

17. A method for diagnosing sleep disorders of a human being having a head having a nose and nostrils therein with the use of self-contained apparatus solely carried by the human body and a mouth and first and second eyes and first and second ears comprising sensing turbulence and/or pressure changes in the respiratory airflow from the nose and/or mouth of the patient, generating a resonant frequency in response to sensing turbulence and/or pressure changes in the respiratory airflow and providing an electrical output and utilizing the electrical output to provide a real time signal which is indicative of breathing of the patient.

18. A method as in claim 17 further including the steps of ascertaining a plurality of events with respect to the patient and having event values which are based upon a minimum duration of time and further including the step of summing the event values and dividing the sum of the event values by the duration of sleep to provide an enhanced respiratory disturbance index RDIplus.

19. A method as in claim 18 together with the step of sensing EEG signals from the brain of the patient and utilizing them in the real time signal.

20. A method as in claim 18 together with the step of sensing eye movement of the patient and providing an electrical signal which is used to provide an event value in the real time signal.

21. A method as in claim 17 together with the step of measuring movement of the trachea and providing an electrical output a real time signal.

22. A method as in claim 17 together with the step of measuring the heart rate of the patient and providing an electrical signal which is utilized in the real time signal.

* * * * *